United States Patent
Bonutti

(10) Patent No.: US 10,294,455 B2
(45) Date of Patent: May 21, 2019

(54) METHODS OF BUILDING A BODY PORTION

(71) Applicant: P Tech, LLC, Effingham, IL (US)

(72) Inventor: Peter M. Bonutti, Delray Beach, FL (US)

(73) Assignee: P Tech, LLC, Effingham, IL (US)

( * ) Notice: Subject to any disclaimer, the term of this patent is extended or adjusted under 35 U.S.C. 154(b) by 393 days.

(21) Appl. No.: 13/912,717

(22) Filed: Jun. 7, 2013

(65) Prior Publication Data
US 2013/0267026 A1    Oct. 10, 2013

Related U.S. Application Data

(63) Continuation of application No. 11/926,609, filed on Oct. 29, 2007, now abandoned, which is a (Continued)

(51) Int. Cl.
*C12N 5/0789*    (2010.01)
*C12N 5/077*    (2010.01)
(Continued)

(52) U.S. Cl.
CPC .......... *C12N 5/0654* (2013.01); *A61F 2/0077* (2013.01); *A61F 2/02* (2013.01);
(Continued)

(58) Field of Classification Search
CPC .......... A61F 2/0063; A61F 2/04; A61F 2/042; A61F 2002/048; A61M 1/14;
(Continued)

(56) References Cited

U.S. PATENT DOCUMENTS 4,292,916 A    10/1981    Bradley
4,311,659 A *   1/1982    Rey .......................... A61F 2/04
                                                              264/221

(Continued)

FOREIGN PATENT DOCUMENTS

GB    2410115 A    7/2005
WO    199001521    2/1990
(Continued)

OTHER PUBLICATIONS http:/dictionary.reference.com/browse/biofilm, printed Jul. 25, 2011.
(Continued)

*Primary Examiner* — Brian E Pellegrino

(57) ABSTRACT

An improved method of implanting cells in the body of a patient includes positioning viable cells on a support structure. One or more blood vessels may be connected with the support structure to provide a flow of blood through the support structure. A support structure may be positioned at any desired location in a patient's body. The support structure may be configured to replace an entire organ or a portion of an organ. An organ or portion of an organ may be removed from a body cells and/or other tissue is removed to leave a collagen matrix support structure having a configuration corresponding to the configuration of the organ or portion of an organ. Alternatively, a synthetic support structure may be formed. The synthetic support structure may have a configuration corresponding to a configuration of an entire organ or only a portion of an organ.

47 Claims, 3 Drawing Sheets

Related U.S. Application Data continuation of application No. 10/457,100, filed on Jun. 6, 2003, now Pat. No. 7,299,805.

(60) Provisional application No. 60/387,013, filed on Jun. 7, 2002.

(51) Int. Cl.

| | |
|---|---|
| *A61F 2/00* | (2006.01) |
| *A61F 2/46* | (2006.01) |
| *C12N 5/00* | (2006.01) |
| *A61F 2/02* | (2006.01) |
| *C12N 5/071* | (2010.01) |
| *A61L 24/00* | (2006.01) |
| *A61L 24/08* | (2006.01) |
| *A61F 2/28* | (2006.01) |

(52) U.S. Cl.
CPC .............. *A61F 2/28* (2013.01); *A61F 2/4601* (2013.01); *A61L 24/0015* (2013.01); *A61L 24/08* (2013.01); *C12N 5/0062* (2013.01); *C12N 5/0068* (2013.01); *C12N 5/0691* (2013.01); *A61F 2002/2817* (2013.01); *A61F 2002/2835* (2013.01); *A61F 2210/0004* (2013.01); *C12N 2501/10* (2013.01); *C12N 2501/105* (2013.01); *C12N 2501/11* (2013.01); *C12N 2501/135* (2013.01); *C12N 2501/155* (2013.01); *C12N 2513/00* (2013.01); *C12N 2533/54* (2013.01); *C12N 2533/90* (2013.01); *Y10S 623/92* (2013.01)

(58) Field of Classification Search
CPC ......... A61M 2210/1082; A61K 35/545; A61L 27/3821; A61L 27/24; A61L 27/365; Y10S 623/92
USPC ............ 623/23.72–23.76; 435/377, 395–403
See application file for complete search history.

(56) References Cited

U.S. PATENT DOCUMENTS

| | | |
|---|---|---|
| 4,352,883 A | 10/1982 | Lim |
| 4,374,699 A | 2/1983 | Sanders et al. |
| 4,412,947 A | 11/1983 | Cioca |
| 4,485,096 A | 11/1984 | Bell |
| 4,485,097 A | 11/1984 | Bell |
| 4,554,686 A | 11/1985 | Baker |
| 4,649,108 A | 3/1987 | Blair |
| 4,678,470 A | 7/1987 | Nashef et al. |
| 4,735,083 A | 4/1988 | Tenenbaum |
| 4,794,078 A | 12/1988 | Blair |
| 4,795,467 A | 1/1989 | Piez et al. |
| 4,812,053 A | 3/1989 | Bhattacharjee |
| 4,863,472 A | 9/1989 | Tormala et al. |
| 4,902,295 A | 2/1990 | Walthall et al. |
| 4,903,254 A | 2/1990 | Haas |
| 4,923,810 A | 5/1990 | Walts et al. |
| 4,937,270 A | 6/1990 | Hamilton et al. |
| 4,950,296 A | 8/1990 | McIntyre |
| 4,987,849 A | 1/1991 | Sherman |
| 4,992,226 A | 2/1991 | Piez et al. |
| 5,001,169 A | 3/1991 | Nathan et al. |
| 5,009,888 A | 4/1991 | Dunn |
| 5,017,229 A | 5/1991 | Burns et al. |
| 5,019,505 A | 5/1991 | Ferguson et al. |
| 5,045,283 A | 9/1991 | Patel |
| 5,053,339 A | 10/1991 | Patel |
| 5,058,088 A | 10/1991 | Haas |
| 5,077,215 A | 12/1991 | McAuslan et al. |
| 5,099,859 A | 3/1992 | Bell |
| 5,110,604 A | 5/1992 | Chu et al. |
| 5,131,907 A | 7/1992 | Williams et al. |
| 5,156,957 A | 10/1992 | Reddy et al. |
| 5,162,535 A | 11/1992 | Schena et al. |
| 5,166,351 A | 11/1992 | Schena et al. |
| 5,202,260 A | 4/1993 | Yee et al. |
| 5,204,106 A | 4/1993 | Schepers et al. |
| 5,179,199 A | 6/1993 | Zabrecky et al. |
| 5,219,361 A | 6/1993 | Von Recum et al. |
| 5,228,478 A | 7/1993 | Kleisle |
| 5,228,573 A | 7/1993 | Pavelle |
| 5,236,838 A | 8/1993 | Rasmussen et al. |
| 5,238,821 A | 8/1993 | Barsomian et al. |
| 5,240,832 A | 8/1993 | Kelton et al. |
| 5,241,072 A | 8/1993 | Colon et al. |
| 5,258,288 A | 11/1993 | Wydro et al. |
| 5,278,256 A | 1/1994 | Bellis |
| 5,282,861 A | 2/1994 | Kaplan |
| 5,283,353 A | 2/1994 | Rasmussen et al. |
| 5,290,494 A | 3/1994 | Coombes |
| 5,294,551 A | 3/1994 | Furcht et al. |
| 5,317,987 A | 6/1994 | Muller |
| 5,324,828 A | 6/1994 | Rasmussen et al. |
| 5,343,385 A * | 8/1994 | Joskowicz ............. B25J 9/1664 700/57 |
| 5,344,455 A | 9/1994 | Keogh et al. |
| 5,344,773 A | 9/1994 | Wei et al. |
| 5,354,853 A | 10/1994 | Staveski et al. |
| 5,358,935 A | 10/1994 | Smith et al. |
| 5,370,990 A | 12/1994 | Staniford et al. |
| 5,403,745 A | 4/1995 | Ollington et al. |
| 5,451,661 A | 9/1995 | Wan |
| 5,453,278 A | 9/1995 | Chan et al. |
| 5,462,983 A | 10/1995 | Bloembergen |
| 5,464,439 A | 11/1995 | Gendler |
| 5,487,986 A | 1/1996 | Wan et al. |
| 5,491,227 A | 2/1996 | Casson et al. |
| 5,492,830 A | 2/1996 | Kalwass et al. |
| 5,501,706 A | 3/1996 | Arenberg |
| 5,501,954 A | 3/1996 | Mahr et al. |
| 5,507,813 A | 4/1996 | Dowd et al. |
| 5,512,475 A | 4/1996 | Naughton et al. |
| 5,512,477 A | 4/1996 | Goodrick et al. |
| 5,514,538 A | 5/1996 | Evans et al. |
| 5,531,791 A | 7/1996 | Wolfinbarger, Jr. |
| 5,534,025 A | 7/1996 | Moussy |
| 5,656,450 A | 8/1997 | Boyan et al. |
| 5,685,826 A | 11/1997 | Bonutti |
| 5,700,553 A | 12/1997 | Cohen |
| 5,741,334 A | 4/1998 | Mullon |
| 5,770,417 A | 6/1998 | Vacanti et al. |
| 5,772,594 A | 6/1998 | Barrick |
| 5,772,695 A | 6/1998 | Orton |
| 5,804,178 A | 9/1998 | Vacanti et al. |
| 5,840,576 A | 11/1998 | Schinstine et al. |
| 5,855,610 A | 1/1999 | Vacanti |
| 5,858,747 A | 1/1999 | Schinstine et al. |
| 5,863,296 A | 1/1999 | Orton |
| 5,883,199 A | 3/1999 | McCarthy |
| 5,899,936 A | 5/1999 | Goldstein |
| 5,902,741 A | 5/1999 | Purchio et al. |
| 5,964,933 A | 10/1999 | Nakamura |
| 6,118,845 A | 9/2000 | Simon et al. |
| 6,152,949 A | 11/2000 | Bonutti |
| 6,171,338 B1 | 1/2001 | Talja |
| 6,174,313 B1 | 1/2001 | Bonutti |
| 6,190,610 B1 | 2/2001 | Goldsmith |
| 6,198,794 B1 | 3/2001 | Peshkin |
| 6,221,316 B1 | 4/2001 | Hanggi |
| 6,268,434 B1 | 7/2001 | Tsai |
| 6,287,340 B1 | 9/2001 | Altman et al. |
| 6,312,784 B2 | 11/2001 | Russell |
| 6,323,307 B1 | 11/2001 | Bigg |
| 6,338,730 B1 | 1/2002 | Bonutti et al. |
| 6,352,557 B1 | 3/2002 | Ferree |
| 6,358,266 B1 | 3/2002 | Bonutti |
| 6,406,725 B1 | 6/2002 | Taylor |
| 6,440,164 B1 | 8/2002 | DiMatteo |
| 6,479,064 B1 * | 11/2002 | Atala .................. A61L 27/3604 424/423 |
| 6,493,058 B1 | 12/2002 | Han |

(56) References Cited

U.S. PATENT DOCUMENTS

| | | |
|---|---|---|
| 6,495,368 B1 | 12/2002 | Wallach |
| 6,506,873 B1 | 1/2003 | Ryan |
| 6,554,455 B2 | 4/2003 | Tsai |
| 6,573,340 B1 | 6/2003 | Khemani |
| 6,593,142 B2 | 7/2003 | Kelly |
| 6,626,939 B1 | 9/2003 | Burnside |
| 6,673,339 B1 | 1/2004 | Atala |
| 6,673,463 B1 | 1/2004 | Onishi |
| 6,698,510 B2 | 3/2004 | Serra |
| 6,740,731 B2 | 5/2004 | Bigg |
| 6,767,850 B1 | 7/2004 | Tebbe |
| 6,924,147 B2 | 8/2005 | Kelly |
| 6,986,735 B2 | 1/2006 | Abraham |
| 7,036,452 B1 | 5/2006 | Tester |
| 7,157,048 B2 | 1/2007 | Goldsmith |
| 7,615,373 B2 | 11/2009 | Simpson |
| 2001/0033857 A1* | 10/2001 | Vyakarnam ......... A61F 2/30756 424/443 |
| 2002/0007223 A1* | 1/2002 | Matapurkar ......... A61K 35/545 623/23.65 |
| 2002/0007294 A1 | 1/2002 | Bradbury et al. |
| 2002/0099440 A1 | 7/2002 | Bader |
| 2002/0119437 A1* | 8/2002 | Grooms ................ A61L 2/0082 435/2 |
| 2002/0182241 A1* | 12/2002 | Borenstein ......... A61L 27/3604 424/422 |
| 2003/0010486 A1 | 1/2003 | Serra |
| 2003/0029373 A1 | 2/2003 | Cooperman |
| 2003/0129751 A1* | 7/2003 | Grikscheit ......... A61L 27/3641 435/378 |
| 2003/0166274 A1* | 9/2003 | Hewitt et al. ................. 435/366 |
| 2003/0232198 A1 | 12/2003 | Lamberti |
| 2003/0235119 A1 | 12/2003 | Wien |
| 2004/0034121 A1 | 2/2004 | Nozaki |
| 2004/0072294 A1 | 4/2004 | Baunhut |
| 2005/0124062 A1 | 6/2005 | Subirade |
| 2005/0209687 A1 | 9/2005 | Sitzman |
| 2006/0236913 A1 | 10/2006 | Wills |
| 2007/0059293 A1 | 3/2007 | Atala |
| 2007/0079748 A1 | 4/2007 | Ahmed |

FOREIGN PATENT DOCUMENTS

| | | | |
|---|---|---|---|
| WO | WO 9311225 A1 * | 6/1993 | ......... A61L 27/3821 |
| WO | 2005080964 | 9/2005 | |

OTHER PUBLICATIONS

Chapter 8 "Paper and Paperboard Packaging" Coles, Richard; McDowell, Derek; Kirwan Mark J. (2003). Food Packaging Technology. Blackwell Publishing.

Final Office Action dated Sep. 25, 2015 relating to U.S. Appl. No. 11/926,609, 18 pages.

Non-Final Office Action dated Dec. 3, 2014 relating to U.S. Appl. No. 11/926,609, 13 pages.

Final Office Action dated Aug. 3, 2011 relating to U.S. Appl. No. 11/926,609, 10 pages.

Non-Final Office Action dated Nov. 16, 2010 relating to U.S. Appl. No. 11/926,609, 7 pages.

Non-Final Office Action dated Jan. 29, 2007 relating to U.S. Appl. No. 10/457,100, 13 pages.

Final Office Action dated Aug. 30, 2006 relating to U.S. Appl. No. 10/457,100, 11 pgs.

Non-Final Office Action dated Feb. 9, 2006 relating to U.S. Appl. No. 10/457,100, 8 pgs.

Final Office Action dated May 25, 2018 for U.S. Appl. No. 15/080,113, 7 pages.

* cited by examiner

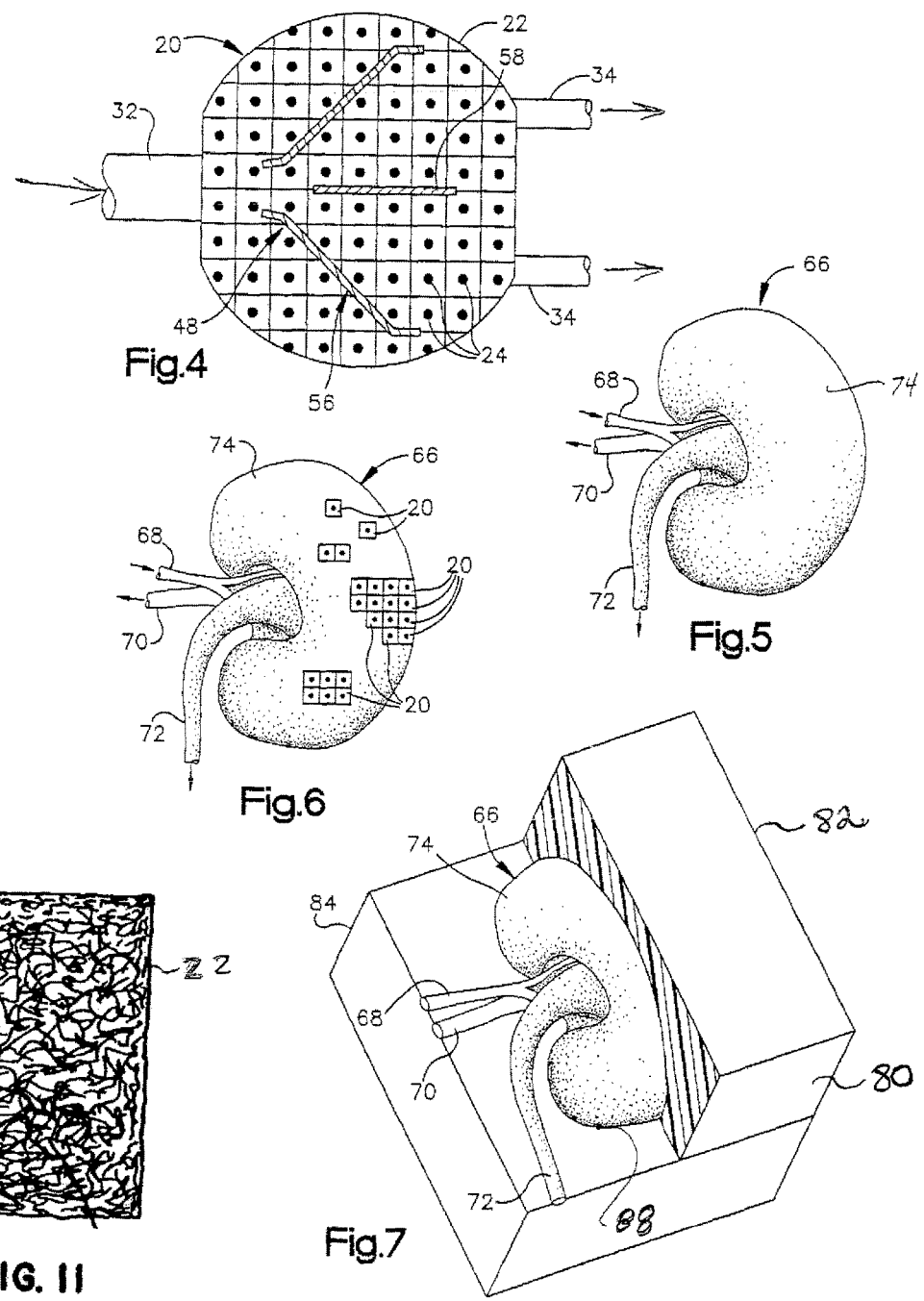

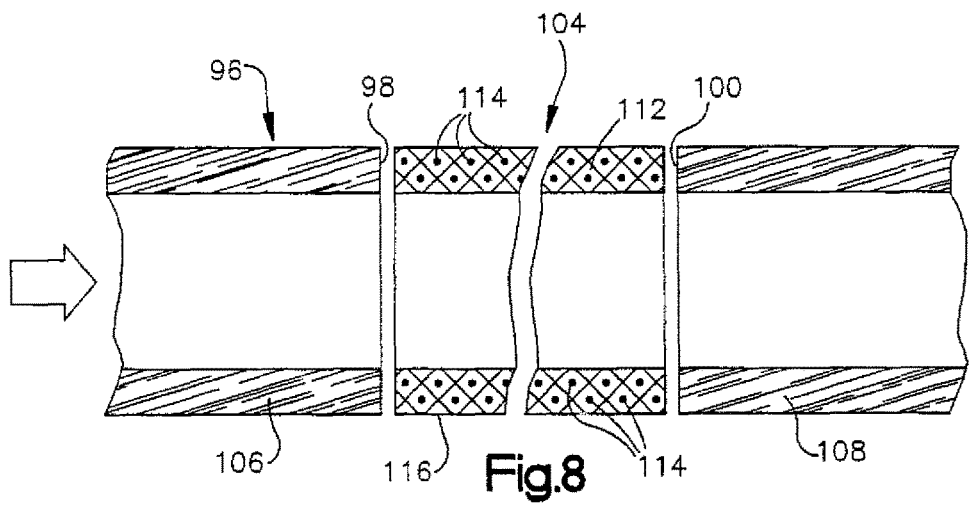
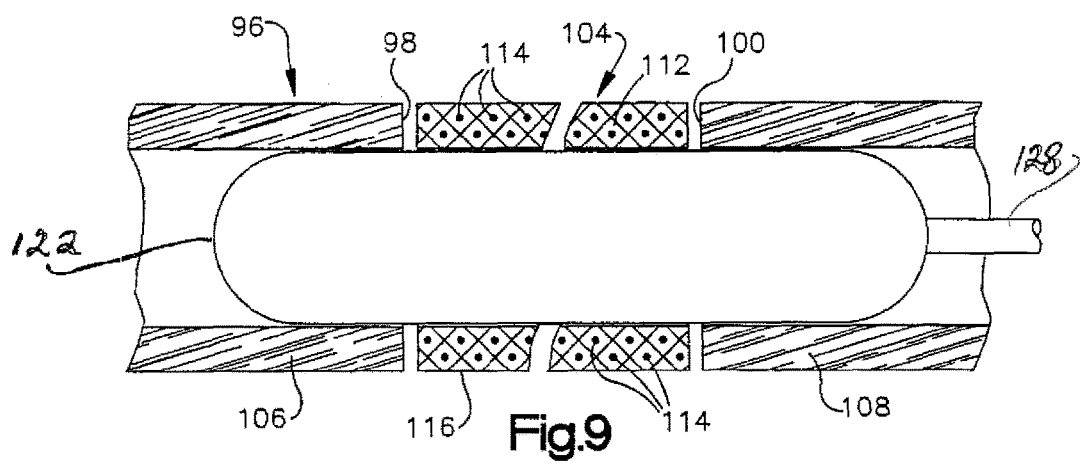
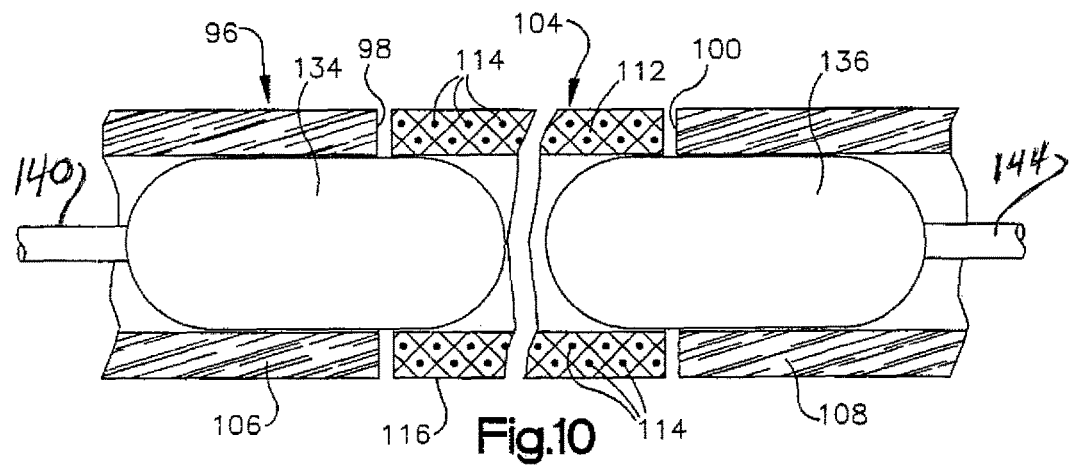

METHODS OF BUILDING A BODY PORTION

CROSS-REFERENCE TO RELATED APPLICATIONS

This application is a continuation of U.S. patent application Ser. No. 11/926,609, filed Oct. 29, 2007, which is a continuation of U.S. patent application Ser. No. 10/457,100, filed Jun. 6, 2003, now U.S. Pat. No. 7,299,805, which claimed the benefit under 35 U.S.C. § 119(e) of Provisional Application No. 60/387,013 filed Jun. 7, 2002, each of which is hereby incorporated by reference in its entirety.

BACKGROUND

The present invention relates to the implanting of cells into a body of a patient, and in particular to the implantation of viable cells on a scaffold or support structure.

Various organs or other tissue in a patient's body may become defective due to trauma, disease, or other causes. Transplanting of organs and/or tissue has been utilized for the treatment of defective organs. However, problems have been encountered in securing an adequate number of suitable donor organs. It is believed that it may be desirable to have a patient grow a replacement organ, portion of an organ, or other body tissue for replacement of any defective tissue, organ, or portion thereof.

SUMMARY

The present invention relates to a method of implanting viable cells into a body of a patient. The viable cells may be positioned on a support structure. One or more blood vessels in a patient's body may be connected with the support structure at one or more locations. The viable cells on the support structure may be exposed to blood flow in the support structure. One or more support structures may be provided and positioned in the patient's body.

The support structure may be formed in many different ways. One way in which the support structure may be formed is by removing an organ or a portion of an organ from a body, either the patient's own body or another body. Cells and/or other tissue may be removed from the organ or portion of an organ to leave a collagen matrix support structure having a configuration corresponding to the configuration of the organ or portion of an organ. Viable cells are positioned on the collagen matrix support structure. The support structure, which has a configuration corresponding to the configuration of an organ or portion of an organ, is positioned in the patient's body with the viable cells disposed on the support structure. Blood vessels may be connected with the support structure as it is positioned in the patient's body.

The support structure may be formed by using an organ or portion of an organ from a body that is either the patient's body or another body as a pattern. Alternatively, the pattern may be synthetically constructed to have a configuration corresponding to the general configuration of an organ or portion of an organ in a patient's body. The pattern may be at least partially enclosed with mold material. The pattern and mold material are subsequently separated to leave a mold cavity. The synthetic support structure is subsequently shaped in the mold cavity. The synthetic support structure may be formed as a unitary member or formed by one or more intertwined strands.

One or more expandable members may be utilized to align an implant and tissue in a patient's body. For example, one or more balloons may be utilized to align a portion of a blood vessel with a segment which is to be implanted into the blood vessel.

It should be understood that the present invention has a plurality of different features which may be utilized separately or in various combinations. It is also contemplated that the various features of the invention may be utilized with known features from the prior art. Although specific combinations of features have been described herein, it is contemplated that other combinations of features will be apparent to those skilled in the art and will be formed.

BRIEF DESCRIPTION OF THE DRAWINGS

The foregoing and other features of the invention will become more apparent upon a consideration of the following description taken in connection with the accompanying drawings wherein:

FIG. 4 is a fragmentary schematic sectional view, generally similar to FIG. 3, depicting the manner in which a plurality of blood vessels are connected with a support structure containing a barrier to direct a flow of blood through the support structure and to disperse the flow of blood in the support structure;

FIG. 5 is a schematic illustration of an organ, that is, a kidney, in a patient's body;

FIG. 6 is a schematic illustration depicting the manner in which a plurality of the support structures of FIGS. 1-4 may be positioned in the organ of FIG. 5;

FIG. 7 is a schematic illustration depicting the manner in which an organ or model of an organ may be used as a pattern to form a mold cavity in which a synthetic support structure may be formed;

FIG. 8 is a schematic illustration depicting the manner in which a support structure on which viable cells are disposed is utilized to replace a portion of a blood vessel;

FIG. 9 is a schematic illustration depicting the manner in which a balloon is utilized to align the support structure and portions of a blood vessel;

FIG. 10 is a schematic illustration, generally similar to FIG. 9, illustrating the manner in which a plurality of balloons may be utilized to align the support structure and portions of a blood vessel;

FIG. 11 is a top view of an embodiment of a support structure in the form of a three dimensional mesh of fibers.

DETAILED DESCRIPTION

General Description

Figure 1:
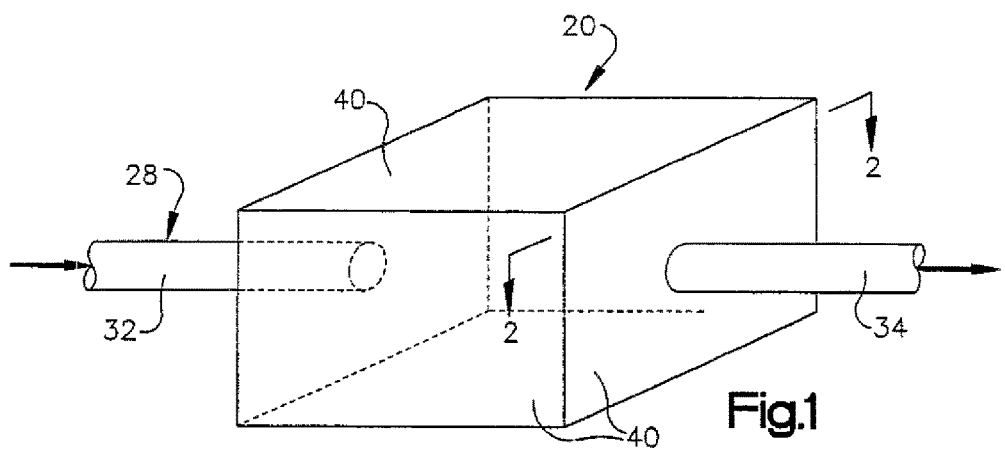
FIG. 1 is a schematic illustration depicting the manner in which a support structure is connected with portions of one or more blood vessels in a patient's body.
Figure 2:
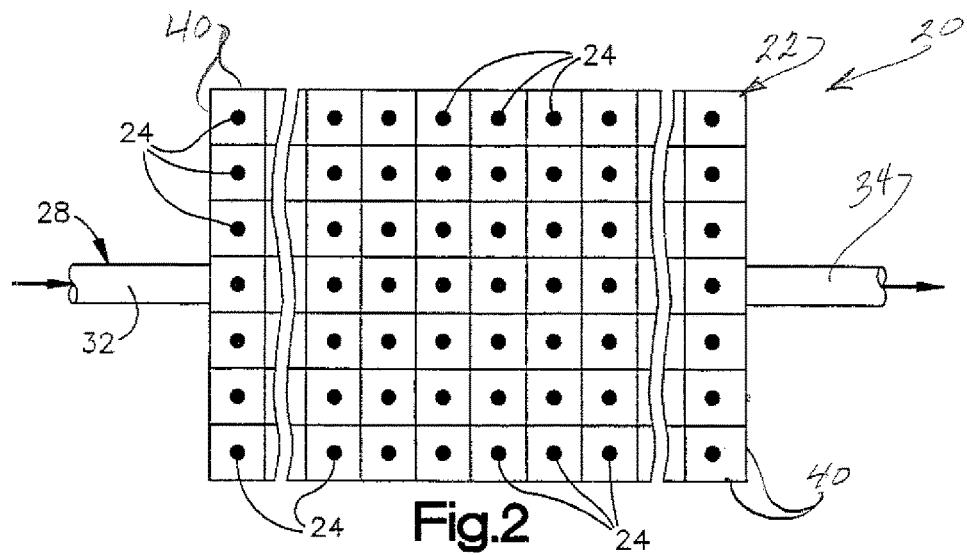
FIG. 2 is a fragmentary schematic plan view, taken generally along the line 2-2 of FIG. 1, illustrating in the manner in which viable cells may be positioned on the support structure of FIG. 1 and exposed to a flow of blood through the support structure.

An implant 20 is illustrated schematically in FIGS. 1 and 2. The implant 20 includes a support structure or matrix 22 (FIG. 2) which may have any desired configuration. A plurality of viable cells 24 (FIG. 2) are positioned on the support structure 22. Although the support structure 22 has been illustrated schematically in FIGS. 1 and 2 as having a rectangular configuration and the viable cells 24 have been illustrated schematically as being disposed in a rectangular array on a rectangular matrix, it is contemplated that the support structure 22 could have any desired configuration and that the viable cells 24 could be disposed in any desired arrangement on the support structure.

In accordance with one of the features of the present invention, one or more blood vessels 28 are connected with the support structure 22 to provide for a flow of blood through the support structure. Although the support structure 22 may be connected with blood vessels 28 in many different ways, in the specific arrangement illustrated in FIGS. 1 and 2, an arteriole (a small artery) 32 and a venule (small vein) 34 are connected with the support structure 22. This results in a flow of blood from left to right, as indicated by arrows in FIGS. 1 and 2, through the implant 20. The viable cells 24 are exposed to the flow of blood.

Although the implant 20 has been illustrated in FIGS. 1 and 2 as being connected with an artery 32 and vein 34, it is contemplated that the implant 20 could be connected with one or more arteries or one or more veins. Thus, a portion of the same artery or vein may be connected with opposite sides of the implant 20. Alternatively, a portion of one artery or vein may be connected with one side of the implant 20 and a portion of another artery or vein may be connected with the opposite side of the implant.

If desired, a plurality of portions of arteries and/or veins may be connected with one side of the implant 20. Similarly, a plurality of portions of arteries and/or veins may be connected with the opposite side of the implant 20. The number of portions of arteries and/or veins connected with the implant 20 will vary depending upon the location where implant 20 is to be positioned in a patient's body. The patient is a living human.

The interior of the support structure 20 has a plurality of passages through which blood may flow. It is contemplated that capillaries, arterioles, and/or venules may grow in the support structure 20. The outer sides of the support structure 20 may be formed of a material which is impervious to blood or a material which restricts the flow of blood from the implant 20 to surrounding tissue.

The implant 20 may be positioned at any desired location in a patient's body. For example, the support structure 22 may be positioned in an organ, that is, a functional unit of cells. The organ in which the support structure 22 is positioned may be a heart, blood vessel, brain, intestine, stomach, adrenal gland, liver, pancreas, skeleton, spinal cord, or other organ. The support structure 22 may be positioned in either soft tissue or hard tissue.

The support structure 22 may have a configuration corresponding to the configuration of an entire organ or a portion of an organ. If the support structure 22 has a configuration corresponding to the configuration of a portion of an organ, a plurality of the support structures 22 may be positioned in an organ. The support structures 22 may be positioned adjacent to each other and/or spaced apart from each other in the organ. Although it may be desired to position the support structure 22 in an organ, the support structure may be positioned at other locations in a patient's body.

The support structure 22 may be positioned in a patient's body by fiber optic surgery, such as arthroscopic or laproscopic surgery. It is contemplated that an imaging apparatus and/or a robotic mechanism may be used in positioning the support structure. This may include moving the support structure through a cannula in the manner disclosed in U.S. patent application Ser. No. 10/102,413 filed Mar. 20, 2002 by Peter M. Bonutti and entitled Methods of Securing Body Tissue. The implant 20 may be connected with tissue in a patient's body in any one of the ways disclosed in the aforementioned application Ser. No. 10/102,413, which is incorporated herein.

The support structure 22 may be formed in many different ways and of many different materials. The specific manner in which the support structure 22 is formed will be influenced, to some extent at least, by the location at which the support structure is to be positioned in the patient's body. In addition, the manner in which the support structure is formed will depend upon the overall size of the support structure and whether or not it is to be formed of biodegradable or nonbiodegradable material.

The support structure 22 may be integrally formed as one piece and have a porous construction with openings in which viable cells 24 are positioned. Alternatively and as shown in FIG. 11, the support structure may be formed by intertwining one or more strands (filaments) of a desired material. The viable cells 24 will be positioned in openings disposed between the intertwined strands.

The support structure 22 may be formed of a hydrophilic material which absorbs body fluid when the support structure 22 is positioned in a patient's body. When the support structure absorbs body fluid, it expands and presses against adjacent body tissues to promote the formation of a mechanical interlock between the support structure 22 and adjacent body tissues. As the hydrophilic material of the support structure absorbs liquid from the patient's body, the volume of the support structure 22 increases. The resulting expansion of the support structure 22 presses the support structure against adjacent body tissue. As this occurs, the material of the support structure 22 and the adjacent tissue are pressed firmly against each other to form a connection between the support structure and the adjacent tissues.

The formation of a mechanical interlock may also be promoted by compressing the support structure 22 before insertion of the support structure into the patient's body. When this is done, the support structure forms a mechanical interlock with tissue due to the combined effects of absorbing fluid and resiliently expanding.

The support structure 22 may be formed of a polymeric material which absorbs body liquid. The polymeric material may be either a copolymer or a dipolymer. The polymeric material may be natural or synthetic collagen. If desired, the polymeric material may be cellulose, petroylglutamic acid, high purity carboxymethylcellulose, or polylactide. Of course, the support structure 22 may be formed of other know material which absorbs body liquid. The support structure 22 may be formed of materials disclosed in U.S. Pat. No. 6,152,949 and form an interlock with adjacent body tissues in the manner disclosed in that patent.

The implant 20 may be formed as an entire organ or as a portion of an organ. When this is the situation, the support structure 22 may be formed by removing an entire organ or a portion of an organ from a body. The body from which the organ is removed may be either the patient's body or another body.

Once the entire organ or portion of an organ has been removed from a body, cells and/or other tissue may be removed from the organ to leave a support structure 22 having a configuration corresponding to the configuration of the organ or portion of an organ. The support structure 22 may include a collagen matrix formed by tissue of the organ or portion of an organ removed from a body.

Rather than using an organ or a portion of an organ removed from a body to form the support structure 22, the organ or portion of an organ may be used as a pattern in the formation of a synthetic support structure. The synthetic support structure 22 may be either biodegradable or non-biodegradable. The synthetic support structure 22 may be molded or woven to have a configuration corresponding to the configuration of the organ or portion of an organ. It is contemplated that the synthetic support structure 22 may have a composite construction and be formed of different materials which have different characteristics.

It is contemplated that the viable cells 24 may be any desired type of viable cells. It is contemplated that the viable cells 24 may correspond to cells which were in a damaged organ or other portion of a patient's body. More than one type of viable cell 24 may be positioned on the same support structure 22. The support structure 22 and viable cells 24 may be positioned in either hard or soft tissue.

When the support structure 22 is to be positioned in an organ, it is contemplated that the viable cells 24 on the support structure 22 will have characteristics associated with the characteristics of normal cells in the organ in which the support structure is to be positioned. Many organs contain cells which have different characteristics and perform different functions within the organ. It is contemplated that the viable cells 24 on the support structure 22 may have different characteristics corresponding to the different characteristics of cells of an organ. When the support structure 22 is to be positioned outside of an organ, the cells positioned on the support structure may have any desired characteristic or combination of characteristics.

It is also contemplated that the viable cells can be pluripotent cells that are directed to differentiate into the desired cell type or types. One example of such cells is stem cells. The differentiation can be controlled by applying or exposing the cells to certain environmental conditions such as mechanical forces (static or dynamic), chemical stimuli (e.g. pH), and/or electromagnetic stimuli.

More than one type of cell may be positioned on the support structure 22. The type of cell positioned at a particular location on the support structure 22 will be determined by the orientation of the support structure in a patient's body and by the specific type of tissue desired at a particular location in a patient's body. For example, stromal cells may be positioned at a location where foundation tissue is desired and another type of cell may be positioned at locations where it is desired to have tissue perform a special function.

As previously noted, the present invention envisions harvesting and culturing cells prior to placement within the support structure 22. Although most researchers tend to isolate and grow one basic cell line, it may be beneficial to mix multiple different cell lines together. For example, embryonic cells or fetal cells can be used to grow cartilage or any desired tissue (such as liver or pancreas) and these can be combined with the mature cells of an older individual. The older individual can either be the patient receiving the mixed cells or possibly another healthier individual. Regardless of the source, the net result is a combination of two cell populations, one younger and more vibrant and another which is older, more mature. The younger cells may have more of an ability to differentiate into the desired cell type, while the older cells may have more of the regulatory factors, tissue inductive factors, etc, which would be more likely to guide and control the younger cells.

Growth factors or other therapeutic agents can be added to either or both of the cell types. The addition of the agents can be before and/or after combining the cells. Examples of growth factors that can be used include insulin-like growth factor (IGF-1), fibroblast growth factor (FGF), transforming growth factor (TGF-β), hepatocyte growth factor (HGF), platelet-derived growth factor (PDGF), Indian Hedgehog (Inh) and parathyroid hormone-related peptide (PTHrP), bone morphogenetic proteins (BMPs), and Interleukin-1 receptor antagonist (IL-1ra).

There are many different types of cells which may be positioned on the support structure 22. These cells include progenitor cells which differentiate and proliferate to form cells having desired characteristics; stromal cells which relate to foundation supporting tissue; and mesenchymal cells which relate to connective tissues, blood and blood vessels, and other systems. Fibroblasts may be used in the production of connective tissues. Osteoblasts may be used in the production of hard tissue (bone). Myoblasts may be used in the production of muscle.

Specific cells may be used to provide for growth of tissue having a function associated with the cell. These cells may include reticular cells, smooth muscle cells, chondrocytes, retinal cells, endothelial cells, and other known cells.

For example, if cardiac tissue is desired, the cells can include endocardial, myocardial, and pericardial cells. These cells can be layered or otherwise arranged. If cartilage and bone tissue is desired, a combination of chondrocytes (and/or chondroblasts) and osteoblasts, or their precursors can be used.

One source of precursor cells is bone marrow, which contain progenitor cells. These progenitor or stem cells can be treated so as to differentiate into any desired cell type.

Although the present invention anticipates that the cells can be harvested in any desired fashion, and are accordingly not discussed in detail herein, the harvesting of fetal cells deserves special note. Fetal cells can be harvested directly from the fetus in situ using minimally invasive techniques or through procedures such as amniocentesis, chorionic villus sampling (CVS), and other similar methods that do not involve invasive contact with the fetus. Regardless of the harvesting method, image guidance (MRI guidance, ultrasonic guidance, etc) can be used. Computer assisted techniques can be used in conjunction with the image guidance. Additionally, the harvesting can be performed using a robotic or haptic system.

If desired, specific types of fetal cells such as liver, pancreas, or renal cells, etc, could be selectively harvested. The fetus does not necessarily have to be harmed during the harvesting, but can be kept viable. Thus, the fetus does not have to be aborted after obtaining the cells, but actually could be left alive and could be a source for cells possibly through one or multiple aspirations while the fetus is still growing. For example, one may require multiple aspirations of liver cells or neural cells, with multiple cell types at various levels of maturation for the desired graft.

Implant

The implant 20 includes the support structure 22 on which the viable cells 24 are disposed. The viable cells 24 are exposed to a flow of blood between the blood vessels 32 and 34. The blood vessels 32 and 34 are connected with the support structure 22. The blood flows through the blood vessels 32 and 34 in the manner indicated by arrows in FIGS. 1 and 2.

It is contemplated that the blood vessels 32 and 34 may be connected with a support structure 22 in any desired manner. In the specific embodiment illustrated schematically in FIGS. 1 and 2, an end portion of the arteriole 32 is stitched to the support structure 22. Similarly, an end portion of the venule 34 is stitched to the support structure 22. In addition to being connected with the blood vessels 28, the implant 20 may be retained in tissue in a patient's body by stitching the support structure 22 to the tissue in the patient's body.

It is contemplated that the blood vessels 28 may be connected with the support structure in many different ways. For example, the arteriole 32 may be connected with the support structure 22 by an adhesive such as cyanoacrylate (so-called "superglue"), Polylatic acid, or fibrin. Additionally, the modified biofilm discussed below in connection with the attachment of cells to the support structure 22 can be used to couple the arteriole 32 and the support structure 22. Of course, the end portion of the venule 34 may be connected with the support structure 22 by an adhesive in the same manner as in which the arteriole 32 is connected with the support structure. It should be understood that the blood vessels 32 and 34 could both be arterioles or venules if desired.

To facilitate connecting the arteriole 32 and venule 34 with the support structure 22, appropriately shaped and sized recesses may be provided in the support structure 22. These recesses would have an inside dimension which is only slightly larger than the outside diameter of the arteriole 32 and/or venule 34. The arteriole 32, for example, would be telescopically inserted into the cylindrical recess in the support structure 22. The joint between the support structure and the exterior surface of the arteriole 32 may be sealed with a suitable sealant. It is contemplated that an adhesive could be utilized as the sealant.

In the embodiment illustrated in FIGS. 1 and 2 the arteriole 32 and venule 34 are shown as being axially aligned with each other, that is, they are in a coaxial relationship. However, it is contemplated that the arteriole 32 could be offset to one side, for example, to the left, and the venule 34 offset to the opposite side, for example, to the right, of the central axis of the support structure 32. This would promote a dispersion of the flow of blood from the arteriole in the support structure 22 before the flow of blood entered the venule 34. Of course, this would increase the exposure of the viable cells 24 to the flow of blood.

If desired, the arteriole 32 could be inserted for a substantial distance, into the support structure 22 and the venule 34 inserted for a substantial distance into the support structure 22. If this was done, it is contemplated that the arteriole 32 would be offset from the venule 34. Thus, the arteriole 32 could be offset downward (as viewed in FIG. 2) and the venule 34 offset upward (as viewed in FIG. 2) so that they are not in axial alignment with each other.

By telescopically inserting the arteriole 32 into a cylindrical recess or hole in the support structure 22 for a distance which is more than one half of the thickness of the support structure, the flow of blood would exit the arteriole adjacent to the side of the support structure from which the venule 34 extends, that is, the right side of the support structure 22 (as viewed in FIG. 2). Similarly, the venule 34 would extend telescopically into a recess which extends past the center of the support structure 22. This would result in the flow of blood in the support structure 22 entering the venule 34 adjacent to the left (as viewed in FIG. 2) side of the support structure 22.

If this was done, the arteriole 32 and venule 34 would not be axially aligned with each other but would be offset so that the blood would flow from the arteriole 32 in a reverse direction, that is toward the left as viewed in FIG. 2, to the entrance to the venule 34. This would result in the arteriole 32 and venule 34 being disposed in a side-by-side and offset relationship relative to each other in the support structure 22. The blood would flow from the end of the arteriole 32 adjacent to the right (as viewed in FIG. 2) side of the support structure 22 to the end of the venule 34 adjacent to the left (as viewed in FIG. 2) side of the support structure. The resulting nonlinear flow of blood between the arteriole 32 and venule 34 would promote dispersion of the blood in the support structure 22 and promote exposure of the viable cells 24 to the flow of blood.

In the embodiment illustrated in FIGS. 1 and 2 the arteriole 32 and venule 34 are connected directly to the support structure 22. However, it is contemplated that the support structure 22 could be provided with a pair of conduits which are connected between an artery and vein in a patient's body. Thus, the support structure 22 may be provided with a tubular conduit in place of the arteriole 32 of FIGS. 1 and 2 and a tubular conduit in place of the venule 34. The tubular conduit which replaces the arteriole 32 would be connected with an artery in the patient's body and the tubular conduit which replaces the venule 34 would be connected with a vein in the patient's body. The tubular conduits which extend from the support structure 22 may be formed of a synthetic material or may be formed by veins and/or arteries harvested from the patient's body or from another body.

A plurality of support structures 22 may be implanted into a patient's body. If this is done, the plurality of support structures 22 may be interconnected by conduits before being placed in the patient's body. The plurality of the support structures 22 may be interconnected to have parallel and/or series flow of blood through the support structures 22.

It is contemplated that feeder conduits could extend from a manifold conduit to conduct a flow of blood to each support structure 22 of a plurality of support structures. If this is done, a second plurality of feeder conduits may extend from a second manifold conduit to each of the support structures to conduct a flow of blood from the plurality of support structures. The first manifold conduit may be connected in fluid communication with an artery in a patient's body and the second manifold conduit may be connected with a vein in a patient's body. This would enable a plurality of support structures 22 to be supplied with blood conducted from a single connection between the first manifold conduit and an artery. Similarly, blood would flow from the plurality of support structures 22 to a vein through a single connection between a vein and the second manifold conduit. If desired, the first and second manifold conduits could both be connected with either an artery or a vein.

It is believed that interconnecting a plurality of support structures 22 with suitable conduits before the support structures are positioned in a patient's body will facilitate positioning of the support structures. This is because the number of connections which have to be made between the support structures 22 and the blood vessels in the patient's body would be minimized. When a plurality of support structure are utilized they may be interconnected in a parallel blood flow arrangement in the manner previously described or in a series blood flow arrangement before being positioned in the patient's body.

It is contemplated that the sides of the support structure 22 may be constructed as to retard a flow of blood from the support structure. Thus, the support structure 22 may be constructed with outer side surfaces that effectively block a flow of blood from the support structure through the outer side surfaces of the support structure. Alternatively, the outer sides of the support structure 22 may be provided with very small openings which effectively retard, without completely blocking, a flow of blood through the sides of the support structure. In another embodiment, the sides of the support material 22 are made of a material that has one-way permeability. This would either allow absorption of blood while preventing discharge, or allow blood discharge while preventing absorption.

If the side walls 40 are effective to block the flow of blood from the support structure 22, all of the blood which enters the support structure 22 from the arteriole 32 (FIGS. 1 and 2) would flow from the support structure through the venule 34. However, if the side walls 40 are somewhat porous so that they are effective to retard or only partially block a flow of blood through the side walls 40, a portion of the blood from the arteriole 32 would flow from the support structure 22 through the side walls 40 of the support structure while the remainder of the blood from the arteriole 32 would flow from the support structure through the venule 34. By allowing some, but not all, of the blood to flow from the support structure 22 through the side walls 40, dispersion of blood within the support structure is promoted.

It is contemplated that minute passages may be provided in the support structure 22 to accommodate the growth of capillaries within the support structure. Thus, a network or web of capillaries may grow in the support structure 22 between the arteriole 32 and venule 34. This network of capillaries would facilitate supplying blood to all of the viable cells 24 within the support structure 22. The side walls 40 (FIG. 1) of the support structure 22 may have small openings through which capillaries grow between the support structure and surrounding tissue in the patient's body.

In the embodiment of the invention illustrated in FIGS. 1 and 2, a single arteriole 32 is connected with a support structure 22 to conduct blood to the support structure and a single venule 34 is connected with the support structure to conduct blood from the support structure. It is contemplated that a plurality of arterioles 32 and/or venules 34 may be connected with the support structure 22. Thus, a plurality of arterioles 32 may be connected with a first side wall 40 of the support structure 22 to conduct a flow of blood into the support structure at a plurality of locations. Similarly, a plurality of venules 34 may be connected with a second side wall 40 of the support structure 22 at a plurality of locations to conduct blood from the support structure. The number of arterioles 32 connected with the support structure 22 may be the same as, greater than, or less than the number of venules 34 connected with the support structure.

When it is desired to conduct blood to and from the support structure 22 along a plurality of flow paths, it is believed that it may be desired to connect a plurality of conduits with the support structure before the support structure is positioned in the patient's body. Thus, at a location remote from an operating room, a plurality of conduits may be connected with one of the side walls 40 of the support structure 22. These conduits may all be connected with a single relatively large conduit. This relatively large conduit would be connected with an artery in a patient's body in an operating room. Similarly, a plurality of conduits may be connected with a second side wall of the support structure 22 and be connected with a second single conduit. This single conduit may be connected with a vein in a patient's body in an operating room. This would minimize the number of connections which would have to be made with the support structure 22 during a surgical procedure in an operating room and would enable most of the connections to be made in a less stressful environment remote from the operating room.

Tissue inductive growth factors and/or other therapeutic agents may be provided on the support structure 22 to promote a growth of tissue between the patient's body and the support structure 22. The tissue growth inductive factors may promote a growth of blood vessels, such as capillaries, between tissue and the patient's body and the support structure 22. The tissue inductive growth factors may also promote the growth of connective tissue between the support structure 22 and the tissue in the patient's body to securely connect the support structure in place in the patient's body.

Other additives include materials such as plasticizers, citrate esters, hexametholsebacate, antibiotics (e.g., tetracyclines, penicillins, mefronidazole, clindamycin, etc.), to prevent infection, etc., or to accomplish other desired conditions or results. Additional additives or therapeutic agents include osteoinductive, biocidal, or anti-infection substances. Suitable osteoinductive substances include, for example, growth factors. The growth factors may be selected from the group of IGF (insulin-like growth factors), TGF (transforming growth factors), FGB (fibroblast growth factors), EGF (epidermal growth factors), BMP (bone morphogenic proteins), and PDGF (platelet-derived growth factors).

The therapeutic agent(s) may be contained within the material of the support structure 22. Alternatively, the agent(s) may be disposed in a structure which is separate from the support structure 22. For example, tissue inductive growth factors could be disposed in a collagen sponge which is positioned adjacent to the support structure 22 in the patient's body. Alternatively, the agent(s) may be positioned in a structure which is connected to the support structure 22.

It is believed that it may be advantageous to have a slow release of the agent(s) adjacent to the patient's body tissue and the viable cells 24. The agent(s) could be held in a biodegradable container or containers which degrade over a period of time and slowly release the agent(s).

In order to promote the attachment of the viable cells to the support structure 22, the support structure 22 can be pretreated with an agent that promotes cell adhesion. One such agent is an organic substance based on a biofilm. A biofilm is a slimy, glue-like substance that forms when bacteria attach to surfaces exposed to water. Typically, colonies of biofilm bacteria are unwanted as they carry out a variety of detrimental reactions. However, a sterile biofilm may be used to promote initial attachment of cells to the support structure 22.

The sterile biofilm could be engineered to isolate the glue-like substance while eliminating the adverse properties of the bacteria. The resulting sterile glue-like substance would be used to help the cells stick to the support structure 22. The engineered biofilm could be added to the support structure 22 in the laboratory that produces the support structure or just prior to the addition of the cells by the user. Alternatively, the biofilm and support structure could be combined intra-corporally.

This biofilm also could be used as an independent polysaccharide based adhesive with mild to moderate adhesion forces. The biofilm could serve as a surgical adhesion or grouting for cells, for tissue fixation (soft tissue to soft tissue, soft tissue to bone, etc.) and as a sealant.

In addition to coating the support structure 22, the biofilm could be used in conjunction with other implants and devices. For example, the biofilm could be used to coat a stent. Although the biofilm might degrade in vivo, the coating could serve as a top coat covering a layer of a therapeutic agent or be impregnated with the therapeutic agent. Thus, as the coating dissolves, the agent is delivered locally in a time-released fashion.

It is contemplated that the support structure 22 may be formed of a biodegradable material. The biodegradable material would at least partially degrade after the patient's body tissue has grown into the support structure 22. The support structure 22 may be formed of a plurality of materials. Some of these materials may be biodegradable and some of the materials may not be biodegradable. But by forming the support structure 22 as a composite of both biodegradable and nonbiodegradable materials, a portion of the support structure would degrade with passage of time while another portion of the support structure would remain.

When the support structure 22 is formed entirely of biodegradable materials, it is contemplated that portions of the structure may degrade before other portions. Thus, one portion of the support structure 22 may be formed of material which degrades over a relatively long period of time while other portions of the support structure 22 may be formed of materials which degrade over a shorter period of time. The provision of tissue inductive growth factors on the support structure would promote the growth of tissue into the support structure during the degradation of material of the support structure.

It is contemplated that the support structure 22 may be relatively large and provide for growth of a substantial volume of tissue in a patient's body. Alternatively, the support structure 22 may be relatively small. If a relatively small support structure 22 is utilized, it is believed that a plurality of the support structures may be positioned in a patient's body. The individual support structures of the plurality of support structures may be positioned adjacent to each other or spaced apart from each other.

When the implant 20 is to be positioned relative to the body tissue, the implant may be moved through a cannula, such as the expandable cannula disclosed in U.S. Pat. No. 6,338,730, into the body tissue. An opening for the support structure 22 may be formed in the body tissue utilizing minimally invasive surgical techniques similar to those disclosed in U.S. Pat. No. 6,174,313. The surgical techniques may involve moving one or more devices through an expandable cannula into the body tissue. The devices moved into the patient's body may be guided by using magnetic resonance imaging systems, ultrasonic imaging apparatus, fluoroscopic apparatus and/or other imaging techniques. The fluoroscopic apparatus may have a construction similar to that disclosed in U.S. Pat. Nos. 5,099,859; 5,772,594; 6,118,845 and/or 6,198,794. A plurality of endoscopes may be utilized to generate stereoscopic images, that is, three dimensional images, of an area where the implant 20 is to be positioned. The endoscopes and other imaging devices may be utilized in a manner which is the same as is disclosed in U.S. patent application Ser. No. 10/102,413 filed Mar. 20, 2002 by Peter M. Bonutti and entitled Method of Securing Body Tissue.

During the performance of surgical procedures, a drapery system which extends between the patient and the surgeon may be utilized. The drapery system may include a drape which is either integrally formed as one piece with a surgeon's gown or is formed separately from the surgeon's gown and is connected with the surgeon's gown. The drapery system maintains a sterile field which extends from the surgeon to space adjacent to the patient. This enables the surgeon to move relative to the patient without contaminating the sterile field. The drapery system may be constructed in the manner disclosed in U.S. patent application Ser. No. 10/263,893 filed Oct. 3, 2002 by Peter M. Bonutti and entitled Surgical Draping System.

If a plurality of relatively small support structures 22 are to be positioned in a patient's body, it is believed that it may be desired to interconnect the plurality of support structures with a network of conduits prior to insertion of the support structures into the patient's body. Thus, a relatively large number of support structures 22 may be interconnected by a web of conduits. The resulting mesh or network formed of the plurality of small support structures 22 and conduits may be loosely positioned over soft tissue in a patient's body. Each of the support structures 22 may then be individually implanted or moved into soft body tissue. The webbing of conduits would extend between the individual support structures 22. The webbing of conduits would then be connected with the patient's vascular system.

By having a relatively large number of small support structures 22 interconnected by a webbing or network of conduits before the support structures are positioned relative to a patient's body, the number of connections to the patient's vascular system for a relatively large number of support structures would be minimized. The webbing or network of support structures 22 would be anchored in the patient's body tissue at each location where a support structure was implanted. The webbing of conduits would be effective to conduct a flow of blood to and from the various support structures 22 in the network.

As previously discussed, it should be understood that the viable cells 24 in the plurality of support structures 22 interconnected by the network of blood conduits may be the same type of cells or different types of cells. It is believed that it may be particularly advantageous to have different types of cells in at least some of the support structures 22. For example, one of the support structures 22 may contain viable endocrine cells and another support structure may contain viable stromal cells. Still another support structure may contain viable endothelial cells.

It should also be understood that a plurality of different types of cells may be provided in a single support structure 22. Thus, viable endocrine cells, viable stromal cells, and viable endothelial cells may all be provided in one support structure 22 of the plurality of support structures interconnected by a network of conduits which conduct blood to the support structures.

It is contemplated that the support structure 22 may be configured so as to provide for the positioning of a layer of viable cells 28 in a patient's body. The viable cells may be allograft mesenchymal cells and/or stem cells.

Blood Flow

In the embodiment of the invention illustrated in FIGS. 1 and 2, the flow of blood is conducted from the arteriole 32 to the support structure 22 and from the support structure to the venule 34. The support structure 22 contains a matrix of viable cells 24 (FIG. 2). In the embodiment of the invention illustrated in FIG. 3, blood flow within the support structure 22 is controlled to maximize the exposure of the viable cells 24 to the flow of blood.

Figure 3:
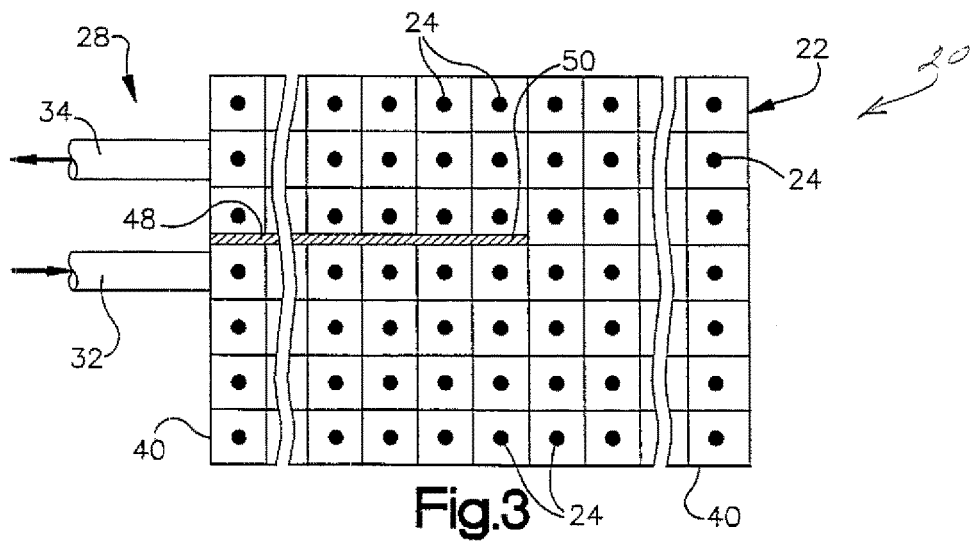
FIG. 3 is a schematic illustration, generally similar to FIG. 2, illustrating in the manner in which a barrier may be used to direct the flow of blood through a support structure.

In the embodiment of the invention illustrated in FIG. 3, an implant 20 includes a support structure 22. Blood vessels 28 are connected with the support structure 22. The blood vessels 28 include an arteriole 32 and a venule 34. In the embodiment of FIG. 3, the arteriole 32 and venule 34 are connected to the same side wall 40 of the implant 20. In order to maximize exposure of the viable cells 24 to a flow of blood, a barrier 48 (FIG. 3) is provided in the support structure 22. The barrier 48 is effective to direct the flow of blood in the support structure 22. The barrier 48 may extend between and be connected with opposite side walls 40 of the support structure 22. Alternatively, the barrier 48 may be spaced from the side walls of the support structure.

It is contemplated that the barrier 48 may be formed of either a material which is impervious to a flow of blood or a material having small openings through which blood can flow. If the barrier 48 is provided with small openings through which blood can flow, the openings would be small enough to retard a flow of blood through the barrier. It is contemplated that barrier 48 may be integrally formed as one piece with a support structure 22 or formed separately from the support structure and mounted in the support structure.

The flow of blood from the arteriole 32 cannot readily move upward (as viewed in FIG. 3) through the barrier 48. Therefore, the blood will flow downward towards the viable cells 24 in the lower portion of the support structure 22. The blood from the arteriole 32 will subsequently flow upward from the lower portion of the support structure toward the upper portion of the support structure. When the blood is has moved around the right (as viewed in FIG. 3) end of the barrier 48, the blood can flow upward through the upper portion of the support structure 22. The upper portion of the support structure 22 is connected with the venule 34 which conducts the flow of blood from the support structure 22 to a vein.

With the specific arrangement of the barrier 48, arteriole 32 and venule 34 illustrated in FIG. 3, it is believed that it would be desired to form the lower side wall 40 of the support structure 22 of a material which blocks or at least substantially blocks a flow of blood. It may also be desired to have the upright (as viewed in FIG. 3) side walls 40 of the retainer of support structure 22 formed of a material which blocks or at least partially blocks a flow of blood. This construction would tend to promote the flow of blood from the lower portion of the support structure 22 to the upper portion of the support structure.

It is contemplated that the barrier 48 may be constructed of a plurality of members which are either interconnected or spaced apart to cause the blood to flow along a convoluted path between the arteriole 32 and venule 34 of FIG. 3. The barrier 48 may be constructed with a plurality of bends which cause the blood to flow from the arteriole 32 through a maze in the support structure 22 to promote the flow of blood past each of the viable cells 24. When the barrier 48 has such an extended irregular configuration, it may be desired to form the barrier 48 of a material through which the blood can flow between various turns and passages in the maze formed within the support structure 22. With a passage of time, it is believed that capillaries may tend to grow in micron size passages in the support structure 22.

In the embodiments of the invention illustrated in FIGS. 1-3, the support structure 22 has been illustrated as having a polygonal configuration, specifically a rectangular configuration. However, it is contemplated the support structure 22 could have a different configuration if desired. For example, rather than the cubicle configuration illustrated in FIGS. 1-3, the support structure could have a configuration of a polyhedron with generally flat sides. Alternatively, the support structure 22 could have a spherical, oval, or ovoid configuration. The specific configuration of the support structure 22 is a function, in part at least, of a location where the support structure is to be positioned in a patient's body. Of course, the configuration of the side walls 40 of the support structure 22 will have an influence on the configuration on the barrier 48. It should be understood that the barrier 48 may have an arcuate configuration and may be formed as a portion of a sphere or cylinder.

Alternative Implant

In the embodiments of the invention illustrated in FIGS. 1-3, the same number of conduits are utilized to conduct blood to the implant as are used to conduct blood from the implant. Thus, a single arteriole 32 and a single venule 34 are connected with a support structure 22 which has a relatively simple cubicle construction. A simple one piece barrier 48 has been illustrated in FIG. 3 to direct a flow of blood within the support structure 22.

In the embodiment of the invention illustrated in FIG. 4, the number of conduits utilized to conduct blood to the implant is different than the number of conduits utilized to conduct blood from the implant. In addition, the implant 20 has a complex configuration formed by flat and arcuate surfaces. A multi-piece barrier is provided in the implant to direct the flow of blood.

In the embodiment of the implant 20 illustrated in FIG. 4, a single arteriole 32 conducts a flow of blood to the support structure 22. A plurality of venules 34 conduct the flow of blood from the support structure 22. Although only two venules 34 have been illustrated in FIG. 4, it should be understood that a greater number of venules may be provided if desired. Of course, a greater number of arterioles 32 could also be connected with the support structure 22 if desired. The number of arterioles 32 may exceed the number of venules 34 if desired.

A plurality of viable cells 24 are provided within the support structure 22. A barrier 48 is provided within the support structure 22. In the embodiment of the invention illustrated in FIG. 4, the barrier 48 is formed of a plurality of pieces or sections. One section 56 of the barrier 48 has a generally conical configuration. However, the section 56 of the barrier 48 has an open left (as viewed in FIG. 4) end portion to enable blood from the arteriole 32 to flow through the leftward end portion of the generally conical section 56 of the barrier. In addition, the barrier 48 includes a flow splitter 58 which disperses a flow of blood entering the open left (as viewed in FIG. 4) end of the conical section 56 of the barrier. The flow splitter section 58 of the barrier may be formed by a plurality of pieces or by a single piece. The flow splitter section 58 may be aligned with the opening in the left end of the barrier 48 or may be offset relative to the opening. For example, the splitter section 58 could be formed by a plurality of spaced apart sections each of which is offset slightly from the central axis of the opening formed in the left (as viewed in FIG. 4) end portion of the section 56 of the barrier 48.

It should be understood that the arteriole 32 and venules 34 may be connected with the support structure 22 of FIG. 4 in any one of the manners previously discussed herein. Rather than connecting an arteriole 32 and venules 34 with the implant 20 as it is positioned in the patient's body, conduits may extend from the support structure 22 and be connected with one or more arteries and/or one or more veins in the patient's body. It should be understood that either a greater or lesser number of arterioles 32 and/or venules 34 may be connected with the support structure 22. The arterioles 32 and venules 34 may be connected with the support structure in any one of the manners previously mentioned herein.

Organ Implant

It is contemplated that the implant 20 of FIGS. 1-4 may be positioned in either soft or hard tissue in a patient's body. It is believed that it may be desired to position one or more of the implants 20 in an organ in a patient's body. If this is done, the implant may be provided with one or more side walls 40 having a configuration which corresponds to a configuration of the exterior surface of the organ.

Although it is contemplated that the implants 20 of FIGS. 1-4 could be utilized in association of any one of the many different organs in a patient's body, the implants are described in conjunction with a kidney 66 (FIG. 5) disposed in the patient's body. It should be understood that the kidney 66 is only an example of one specific organ, that is, a functional unit of cells, with which the implants of FIGS. 1-4 may be associated.

The kidney 66 has a renal artery 68 through which blood is conducted to the kidney. In addition, the kidney 66 has a renal vein 70 through which blood is conducted from the kidney. A ureter 72 conducts urine from the kidney 66 to the patient's bladder. The renal artery 68, renal vein 70 and ureter 72 are connected with a renal capsule 74.

When a kidney 66 becomes damaged by trauma and/or disease, it may be desired to rejuvenate the kidney through the use of one or more implants corresponding to the implants 20 of FIGS. 1-4. The implants 20 may be positioned in a spaced apart relationship in the kidney 66 or positioned adjacent to each other. The specific location and arrangement of the implants 20 in the kidney 66 will depend upon the extent and type of damage which the kidney has incurred.

The size and number of the implants positioned in the kidney 66, as well as their location in the kidney can be varied in the manner believed to be the best remedy for damage to the kidney. For example, a plurality of the implants 20 (FIGS. 1-4) may be positioned at spaced apart locations in the kidney 66 (FIG. 6). Alternatively, the plurality of the implants 20 may be positioned in engagement with each other at selected locations in the kidney 66. Since the implants 20 are relatively small, the locations where they are positioned in the kidney 66 can be selected to best compensate for the damage incurred by the kidney.

When a single implant 20 is to be positioned in the kidney, the implant may be connected with blood vessels in the kidney in the manner previously described in conjunction with FIGS. 1-4 herein. Alternatively, a plurality of the implants 20 may be connected in series with each other so that blood flows from one implant to the next succeeding implant. As was previously mentioned herein, the implants 20 may be connected in parallel with each other and with an artery which supplies blood to the implants and a vein which receives the blood from the implants. As was also previously mentioned, the implants 20 may be associated with any desired organ in the patient's body. The kidney 66 of FIGS. 5 and 6 is only representative of many organs in a patient's body.

When an implant 20 is to be positioned in the kidney 66, a recess or opening having a configuration corresponding to the configuration of the implant is cut into the kidney. The implant 20 is then connected with blood vessels in the kidney 66 and is positioned in the opening (FIG. 6). The opening may be sized so as to accept a single implant 20 or a plurality of implants. If the opening is sized to accept a single implant 20, the size of the single implant may be either relatively small or relatively large depending upon the damage which has been occurred by the kidney.

Under certain circumstances, it is believed that it may be desired to remove a section, that is a relatively large piece of a kidney. When this has been done, a single implant 20 having a configuration corresponding to the configuration of the removed section of the kidney may be implanted at the location where the section was removed from the kidney. Since the relatively large implant 20 has the same configuration as the exterior surface of the kidney, when tissue grows into the implant, the implant will form a portion of the kidney having the same configuration as the section which was removed from the kidney.

When one or more implants 20 are to be positioned in the kidney 66, the viable cells 24 may include renal cells having characteristics of replaced cells in the kidney. Some of the viable cells in the implants 20 may be stromal cells and/or fibroblast. Depending upon the location where the implants 20 are positioned in the kidney, some of the viable cells 24 may be endothelial cells. Thus, stromal cells, renal cells, and endothelial cells may be positioned on a single implant 20 which is connected with the kidney 66. Of course, other types of cells may be positioned on the implant if desired.

Although the implants 20 have been illustrated in FIG. 6 as being positioned in the kidney 66, it is contemplated that the implants 20 may be positioned in a different organ if desired. For example, the implants 20 may be positioned in a patient's heart or one or more of the bones of the patient's skeleton. It is contemplated that the implants 20 may be used for applications other than partial or total organ replacement. Thus, the implant 20 may be located at any desired location in either hard or soft tissue in the patient's body.

Organ Replacement

It is contemplated that it may be desired to replace an entire organ rather than a portion of the organ. When an organ is to be replaced, a support structure 22 having a configuration corresponding to the configuration the organ to be replaced is formed. This support structure 22 may be naturally formed or synthetically formed. The organ to be replaced may be any one of the organs in the patient's body.

Assuming that the kidney 66 is the organ in a patient's body to be replaced, it may be desired to form a support structure having a configuration corresponding to the configuration of the kidney 66. When it is desired to utilize a naturally formed support structure having the configuration of a kidney, a kidney 66 is obtained from a body. The kidney 66 may be obtained from a patient's own body, from the body of another living human, from a cadaver (dead human body), or from a living or dead animal.

When a kidney is used to form the support structure, it may be desired to render the organ non-antigenic. Accordingly, any living cells on a kidney 66 removed from a living donor may be killed with a cytotoxic solution, such as a strong saline solution. Alternatively, the living cells may be killed by radiation. Of course, other methods could be utilized to kill the living cells.

Assuming that the kidney 66 is to be obtained from a cadaver, the renal artery 68, renal vein 70 and ureter 72 are severed and the kidney 66 is removed from the cadaver. Dead cells and/or other tissue are removed from the cadaver kidney to leave a collagen matrix having a configuration corresponding to the configuration of the kidney in the cadaver. The collagen matrix may have a relatively large portion with a configuration corresponding to the configuration of the renal capsule 74 (FIG. 5), and three tubular conduits corresponding to the renal artery 68, renal vein 70 and ureter 72.

The collagen matrix is utilized as a support structure 22 for viable cells, corresponding to the viable cells 24 of FIGS. 1-4. It is contemplated that the viable cells 24 will be different types of cells and will be placed at various locations in the collagen matrix forming the support structure 22 made from the cadaver kidney. For example, renal cells may be positioned in the portion of the collagen matrix formed by the cadaver kidney corresponding to the renal capsule 74. Endothelial cells may also be positioned on the portion of the collagen matrix corresponding to the renal capsule 74 and on the portions of the collagen matrix corresponding to the renal artery 68, renal vein 70 and ureter 72. In addition, stromal cells may be positioned on the portion of the collagen matrix corresponding to the renal capsule 74, renal artery 68, renal vein 70 and ureter 72. Fibroblast and mesenchymal cells may also be placed on the support structure 22 formed from the cadaver kidney. In addition, materials for promoting growth of tissue may be positioned on the support structure.

Once the viable cells 24 have been positioned on the collagen matrix support structure 22 formed from the cadaver kidney, the result is a replacement kidney 66. The replacement kidney 66 may be formed at a location spaced from an operating room. After the replacement kidney 66 has been formed, it may be transported to the operating room and implanted in the patient.

To implant the replacement kidney 66 in the patient, the damaged kidney in the patient is removed. Removal of the damaged kidney 66 from the patient would involve severing the renal artery 68, renal vein 70 and ureter 72 connected with the damaged kidney in the patient.

After the damaged kidney 66 has been removed from the patient, the renal artery 68 of the replacement kidney is connected with the portion of the renal artery remaining in the patient's body. Similarly, the renal vein 70 of the replacement kidney 66 is connected with the portion of the renal vein remaining in the patient's body. In addition, the ureter 72 on the replacement kidney 66 is connected with the portion of the ureter remaining in the patient's body. The replacement kidney 66 is then moved to a desired location in the patient's body.

Blood is conducted to the replacement kidney 66 through the remaining portion of the patient's renal artery 70 and the portion of the renal artery associated with the replacement kidney. Blood is conducted from the replacement kidney 66 through the portion of the renal vein 70 associated with the replacement kidney and the remaining portion of the patient's renal vein. Urine is conducted from the replacement kidney 66 through the portion of the ureter 72 associated with the replacement kidney and to the remaining portion of the patient's ureter.

Although the foregoing description has related to replacement of a kidney 66, the method described herein may be used in association with the replacement of the other organs in a patient's body. Thus, the method described herein may be used in conjunction with the replacement of an adrenal gland, heart, liver, bone, pancreas, or other organ.

Rather than utilizing the collagen matrix of the cadaver kidney to at least partially form the support structure for a replacement kidney, the cadaver kidney may be utilized as a pattern to form a mold cavity having a configuration corresponding to the configuration of the cadaver kidney. Thus, the cadaver kidney 66 (FIG. 7) may be enclosed with mold material 80. The mold material may be divided into two segments 82 and 84 (FIG. 7). The pattern 66 is enclosed by the mold material 80 and the mold material is solidified around the pattern to form the two segments 82 and 84.

Once the mold material has solidified around the kidney pattern 66, the kidney pattern is separated from the mold. Once the kidney pattern 66 has been separated from the mold 62, the two segments 82 and 84 may be interconnected to form a mold assembly which defines a recess or cavity 88. The recess or cavity 88 has a configuration which corresponds to the configuration of the pattern kidney along with the attached portions of the renal artery 68, renal vein 70, and ureter 72.

The kidney pattern 66 may be obtained from a patient, from another living human, from a cadaver, or from an animal. It is believed that it may be preferred not to use the patient's own kidney as the kidney pattern 66 since the configuration of the patient's own kidney may be unsuitable. If desired, an artificial pattern, having a configuration corresponding to a desired configuration of a kidney may be used as a pattern for the mold cavity 88.

Once the mold cavity 88 has been formed by separating the mold segments 82 and 84 from the natural or artificial kidney pattern 66, a synthetic support structure 22 is formed in the mold cavity 88. This may be accomplished by injecting a material into the recess or cavity 88 while the two mold segments 82 and 84 are interconnected. The material injected into the mold cavity 88 may be either biodegradable or nonbiodegradable. The material injected into the mold cavity 88 solidifies with an open cell porous structure. Synthetic collagen or polylatic acid with a chemical blowing agent or entrained gas may be utilized to form the porous support structure.

When the material injected into the mold cavity has solidified with an open cell porous structure, it will have a configuration corresponding to the configuration of the renal capsule 74 of the kidney pattern 66, the renal artery 68, renal vein 70 and ureter 72 connected with the renal capsule of the kidney pattern. The resulting support structure 22 is formed as one piece of porous material.

The selected viable cells, corresponding to viable cells 24 (FIGS. 1-4), are positioned in small openings or pores of the cast porous support structure 22 having the configuration of a kidney. It is contemplated that the viable cells 24 may be positioned in any one of many different known ways on the porous support structure 22 having the configuration of a kidney. One way in which the viable cells may be positioned on the porous support structure 22 is to inject a liquid solution containing the viable cells 24 into the porous support structure 22. The viable cells 24 would be the deposited in the porous of the support structure 22 as the liquid dries. A different solution with different viable cells may be injected in different portions of the porous support structure 22. The viable cells 24 may be any of the viable cells previously mentioned herein. Of course, the viable cells 24 would be deposited on the porous support structure 22 in accordance with the desired tissue structure to be obtained by growth of the viable cells. Other known methods of positioning viable cells on a support structure may be utilized if desired.

Rather than forming a support structure 22 for the synthetic replacement organ of a porous material, it is contemplated that the support structure may be formed of intertwined strands or filaments (FIG. 11). The strands or filaments may be woven together in the recess or cavity 88 formed by the mold segments 82 and 84. This would result in the intertwined filaments or strands having an overall configuration corresponding to the configuration of the pattern kidney 66 of FIG. 7.

The intertwined strands or filaments would define relatively small spaces in which the viable cells 24 would be positioned. The viable cells 24 may be positioned on the woven support structure by injecting a solution containing the viable cells into the spaces or recesses formed by the intertwined strands of the support structure. Of course, different types of viable cells 24 would be positioned at different locations in the woven support structure. Any one of the desired types of viable cells 24 previously mentioned herein may be utilized. It should be understood that the specific viable cells 24 positioned at a specific location on the woven support structure 22 would depend upon the desired characteristics of the tissue to be grown at that location.

The strands of the woven support structure 22 may be either a naturally occurring materials or synthetic materials. The strands of the woven support structure 22 may be biodegradable or nonbiodegradable. It is contemplated that strands of synthetic or natural collagen may be utilized to form the woven support structure 22 on which the viable cells 24 are positioned. If desired, the exterior of the woven support structure 22 may be sealed by encapsulating the woven support structure with a material through which blood cannot easily flow. The material used to encapsulate the woven support structure may be either biodegradable or nonbiodegradable. It is contemplated that a suitable polymeric material, such as polylatic acid, may be utilized. It is believed that blood vessels, such as capillaries, will grow through small passages or channels formed in the woven support structure.

The foregoing description has been a conjunction with the replacement of a kidney 66 in a patient. It is contemplated that the procedures previously described herein could be utilized in conjunction with a replacement of many different types of organs. For example, a patient's pancreas may be replaced. If the patient's pancreas is replaced, viable endocrine cells and viable exocrine cells may be positioned on the support structure 22. In addition, islets of Langerhans could be positioned on the support structure.

It is contemplated that the entire pancreas or only a portion of the pancreas may be replaced. If desired, relatively small implants, corresponding to the implants 20 of FIGS. 1-4, may be positioned in the pancreas. The specific types of viable cells, that is islets of Langerhans, endocrine, and/or exocrine cells would be positioned at the location on the support structure 20 where the corresponding tissues are to be grown.

It is contemplated that a portion of the patient's hard tissue (bone) may be replaced using the foregoing methods. If this is to be done, a support structure 22 having a configuration corresponding to a configuration of at least a portion of one of the bones in the patient's skeleton would be replaced. The viable cells 24 positioned on the support structure 22 may be osteoblasts and/or mesodermal cells. In addition, osteochondral cells may be positioned on the support structure 22. Myoblasts may be utilized in association with the support structure 22 to promote the growth of muscular tissue.

Partial Replacement of an Organ

Rather than replacing an entire organ, it is contemplated that a portion of an organ may be replaced. In FIG. 8, a segment of a blood vessel 96 is to be replaced. However, it should be understood that the method of the present invention may be used to replace portions of an organ other than a blood vessel. The segment of the blood vessel 96 has been selected to be representative of a portion of many different organs in a patient's body.

When a segment of a blood vessel 96 is to be replaced, it is believed that the blood vessel will be severed at cuts 98 and 100 disposed at spaced apart locations along the length of the blood vessel. The portion of the patient's blood vessel between the cuts 98 and 100 is removed. An implant 104 is positioned between the cuts and connected with segments 106 and 108 of the blood vessel 96. The implant 104 is tubular and has a cylindrical configuration.

The implant 104 includes a cylindrical support structure 112 having the same general construction as the support structure 22 of FIGS. 1-4. The support structure 112 has a plurality of openings or recesses in which viable cells 114 are disposed. In the embodiment of FIG. 8, the support structure 112 is enclosed by an outer layer 116 which blocks a radially outward flow of blood from the inside of the tubular cylindrical implant 104.

The segments 106 and 108 of the blood vessel 96 may be connected with the support structure 112 by stitching or by adhesive. Of course, the support structure 112 could be connected with the segments 106 and 108 of the blood vessel 96 in a different manner if desired.

It is contemplated that the viable cells 114 may include endothelial cells, mesenchymal cells, and/or smooth muscle cells. It should be understood that more than one type of cell may be mounted on the support structure 112. Tissue growth induction materials may be provided on the support structure 112 to promote a growth of tissue between the segments 106 and 108 of the blood vessel 96 and the support structure 112. During a flow of blood through the blood vessel 96, the viable cells 114 on the support structure 112 are exposed to the flow of blood.

If the blood vessel 96 is a vein, it may be desired to provide a check valve in association with the implant 104. The check valve may be formed by flexible flaps which are pressed against each other to prevent a back flow of blood in much the same way as in naturally occurring veins. The check valve may be formed by flaps of synthetic material or of a matrix of collagen or other materials in which viable smooth muscle cells are disposed. If viable smooth muscle cells are provided on flaps formed of a support structure of natural or synthetic collagen or other material, viable smooth muscle cells on the support structure 112 and the smooth muscle cells on the check valve may grow together to provide a check valve having the same general construction as a naturally occurring check valve in a vein or other organ.

Rather than being connected with a segment of a blood vessel, one end of the implant 104 may be connected with another organ, such as a heart. Thus, the patient's blood vessel may be severed adjacent to the heart. The segment 106 of the blood vessel would be connected with one axial end portion of the support structure 112 of the implant 104. The opposite axial end portion of the tubular cylindrical implant 104 would be connected directly with the patient's heart. Of course, the implant 104 could be associated with organs other than a patient's heart. It should also be understood that the implant 104 may be positioned in a blood vessel at a location remote from other organs.

During connection of the segments 106 and 108 of the blood vessel 96 with the implant 104, it may be advantageous to utilize an expandable member 122 to align the segments 106 and 108 of the blood vessel 96 with the implant 104 in the manner illustrated schematically in FIG. 9. When the expandable member 122 is in a contracted condition, it is inserted through a relatively small slit in the segment 108 of the blood vessel 96 at a location remote from the cuts 98 and 100 where the implant 104 is to be positioned. The expandable member 122 is moved axially along the blood vessel 96 to a location adjacent to the cut 100. While the expandable member is in a contracted condition, it is moved from the segment 108 of the blood vessel 96 into the implant 104. The leading end portion of the expandable member 122 is then moved from the implant 104 into the segment 106 of the blood vessel 96.

Once the expandable member has been positioned so that it extends between the segments 106 and 108 of the blood vessel 96 and through the implant 104 (as shown in FIG. 9), the expandable member is expanded. As the expandable member 122 is expanded, the end portions of the segments 106 and 108 of the blood vessel 96 adjacent to the implant are expanded and moved into alignment with the implant 104. As the expandable member 122 expands radially outward from a contracted condition to the expanded condition illustrated schematically in FIG. 9, a collapsed or contracted end portion of the segment 106 of the blood vessel 96 adjacent to the cut 98 is expanded. As this occurs, the end portion of the blood vessel segment 106 adjacent to the cut 98 moves radially outward and is aligned with an adjacent end portion of the cylindrical tubular implant 104. At the same time, the opposite end portion of the expandable member 122 is expanded. As this occurs, the end portion of the segment 108 of the blood vessel 96 adjacent to the cut 100 is expanded. Thus, the end portion of the blood vessel 108 is expanded from a collapsed or contracted condition to the expanded condition illustrated in FIG. 9 by expansion of the expandable member 122.

As the expandable member 122 expands, a central portion of the expandable member, that is a portion of the expandable member enclosed by the implant 104, expands into engagement with an inner side surface of the implant 104. As this occurs, annular axially opposite ends of the implant 104 are aligned with the cuts 98 and 100 on the ends of the blood vessel segments 106 and 108.

While the blood vessel segments 106 and 108 are aligned with the implant 104, the cut 98 on the end portion of the blood vessel 106 is connected to the annular end portion of the implant 104. The segment 106 of the blood vessel 96 may be connected with the implant 104 by stitching, by suitable adhesive, or by other known methods. Similarly, the cut 100 on the end portion of the segment 108 of the blood vessel 96 is connected to the implant 104 by stitching, a suitable adhesive, or other known methods.

Once the blood vessel segments 106 and 108 have been connected with the implant 104, the expandable member 122 is contracted. The contracted expandable member 122 is then pulled out of the blood vessel 96 through the same small opening through which the contracted expandable member was moved into the blood vessel.

The expandable member 122 may be expanded by a mechanical device or by fluid pressure. Thus, the expandable member may have a device which expands through a mechanical action in a manner similar to that disclosed in U.S. Pat. No. 5,685,826. Alternatively, the expandable member 122 may be expanded under the influence of fluid pressure in the manner similar to that disclosed in U.S. Pat. No. 6,358,266. The expandable member 122 may be expanded in the manner similar to that disclosed in U.S. Pat. No. 6,338,730.

Although it is believed that many different types of known expandable devices may be utilized for the expandable member 122, the expandable member may be a balloon which is expanded under the influence of either gas or liquid pressure. The gas or liquid pressure may be conducted to the balloon through a conduit 128 (FIG. 9). The conduit 128 may have sufficient rigidity so as to be able to move the expandable member 122, specifically, a balloon, along the blood vessel 96 and through the implant 104 to the position illustrated schematically in FIG. 9 while the expandable member is in a contracted condition.

Once the expandable member has been expanded, under the influence of fluid pressure conducted through the conduit 128, the implant 104 and segments 106 and 108 of the blood vessel 96 are interconnected. The fluid is then exhausted from the expandable member 122 through the conduit 128 to contract the expandable member. The contracted expandable member is then pulled out of the blood vessel 96 under the influence of force transmitted through the conduit 128.

Rather than using a single expandable member 122, a plurality of expandable members 134 and 136 (FIG. 10) may be utilized to align the implants 104 and the end portions 106 and 108 of the blood vessel 96. The members 134 and 136 may be expanded by mechanical mechanisms or may be expanded under the influence of fluid pressure in the manner previously explained in conjunction with the expandable member 122 of FIG. 9.

The expandable member 134 is inserted into the segment 106 of the blood vessel 96 when the expandable member is in a contracted condition. The contracted expandable member 134 is inserted through a small slit formed in the blood vessel 106 at a location spaced from the cut 98. The contracted expandable member 134 is pushed along the segment 106 of the blood vessel by a conduit 140 connected with the contracted expandable member 134. The leading end portion of the contracted expandable member 134 is moved from the segment 106 of the blood vessel 96 into the implant 104.

Similarly, the contracted expandable member 136 is moved into the segment 108 of the blood vessel 96 through a small slit at a location spaced from the cut 100. The contracted expandable member 136 is pushed along the segment 108 of the blood vessel 96 by a conduit 144. The leading end portion of the contracted expandable member 136 is moved from the segment 108 of the blood vessel 96 into the implant 104.

After both of the contracted expandable members 134 and 136 have been position with their leading end portions in the implant 104, they are expanded. Expansion of the expandable member 134 expands the end portion of the blood vessel segment 106 and moves it into alignment with the adjacent end portions of the implant 104. Similarly, expansion of the expandable member 136 expands the end portion of the blood vessel segment 108 and moves it into alignment with the end portion of the implant 104. This results in the implant 104 and the segments 106 and 108 of the blood vessel 96 being held in axial alignment with each other, in the manner illustrated schematically in FIG. 10, by the expanded expandable members 134 and 136.

While the implant 104 and segments 106 and 108 of the blood vessel 96 are held in alignment by the expanded expandable members 134 and 136, the end portions of the segments of the blood vessel are connected with the implant 104. Thus, the annular cut end 98 of the segment 106 to the blood vessel 96 is connected to one annular end of the implant 104. The annular cut end 100 of the blood vessel segment 108 is connected to the opposite annular end of the implant 104. The blood vessel segments 106 and 108 may be connected with the implant 104 by stitches, a suitable adhesive, or another known manner.

Once the blood vessel segments 106 and 108 have been connected with the implant 104, the expandable members 134 and 136 are contracted. The contracted expandable members 134 and 136 are then pulled from the blood vessel segments 106 and 108 through the small slits which they enter the blood vessel segments.

Although the expandable members 134 and 136 may be mechanically expandable members, it is believed that it may be preferred to expand the expandable members under the influence of fluid pressure, that is under the influence of pressure transmitted through either a gas or a liquid. The fluid pressure is conducted to the expandable members 134 and 136 through the conduits 140 and 144.

In the embodiment of the invention illustrated in FIGS. 9 and 10, the expandable members 122, 134 and 136 are illustrated in conjunction with the connecting of segments 106 and 108 with a blood vessel 96 with an implant 104. However, it is contemplated that implant 104 could be connected directly with an organ, such as a heart. For example, if the left (as viewed in FIG. 9) end of the implant 104 is to be connected with a heart, the segment 106 of the blood vessel 96 would be omitted and the left or leading end portion of the balloon 122 (FIG. 9) inserted into an opening formed in the heart. This would align the implant 104 with the opening in the heart. The implant 104 would then be connected directly to the heart with a suitable adhesive, stitching or other known device. The segment 108 of the blood vessel 96 would then be connected with the implant 104 while the expandable member 122 maintains the segment 108 of the blood vessel 96 in alignment with the implant 104.

Although the expandable members 122, 134 and 136 have previously been described herein in conjunction with the connecting of an implant 104 with at least one of the blood vessel segments 106 and/or 108, it is contemplated that the expandable members may be utilized in the positioning many different types of implants relative to many different types of tissue. For example, expandable members similar to expandable members 122, 134 and 136 may be utilized in conjunction with the connection of ducts with organs or with implanting of a segment in a duct. Alternatively, expandable members, similar to the expandable members 122, 134 and 136, may be utilized during the connection of an implant in a portion of a patient's intestine or during the connection of an implant with one end of an intestine and a stomach.

It is contemplated that an implant may be positioned in a bone in a patient's body using expandable members similar to the expandable members 122, 134 and 136. This may be done by inserting an expandable member through an opening in the implant. The expandable member would extend from the implant into the bone to align the bone with the implant. Once the bone and the implant have been interconnected the expandable member would be withdrawn from the opening through which it was inserted into the implant. Once this has been accomplished, the interior of the bone may be filled with an artificial cancellous bone or with a slurry containing osteoblast and bone growth promoting materials.

CONCLUSION

In view of the foregoing description, it is apparent that the present invention provides a method of implanting viable cells 24 into a body of a patient. The viable cells 24 may be positioned on a support structure 22. One or more blood vessels 28 in a patient's body may be connected with the support structure 22 at one or more locations. The viable cells 24 on the support structure 22 may be exposed to blood flow in the support structure. One or more support structures 22 may be provided and positioned in the patient's body.

The support structure 22 may be formed in many different ways. One way in which the support structure 22 may be formed is by removing an organ 66 or a portion of an organ from a body, either the patient's own body or another body. Cells and/or other tissue may be removed from the organ 66 or portion of the organ to leave a support structure 22 having a configuration corresponding to the configuration of the organ or portion of an organ. Viable cells 24 are positioned on the support structure 22. The support structure 22, which has a configuration corresponding to the configuration of an organ 66 or portion of an organ, is positioned in the patient's body with the viable cells 24 disposed on the support structure 22. Blood vessels 28 may advantageously be connected with the support structure 22 as it is positioned in the patient's body. The support structure 22 may correspond to an entire organ 66 or only a portion of an organ.

The support structure 22 may be formed by using an organ 66 or portion of an organ from a body, that is either the patient's body or another body, as a pattern. Alternatively, the pattern may be synthetically constructed to have a configuration corresponding to the general configuration of an organ 66 or portion of an organ in a patient's body. The pattern is at least partially enclosed with mold material 80. The pattern and mold material are subsequently separated to leave a mold cavity 88. The synthetic support structure 22 is subsequently shaped in the mold cavity 88. The synthetic support structure may be formed as a unitary member or formed by one or more intertwined strands.

One or more expandable members 122, 134 and/or 136 may be utilized to align an implant 104 and tissue 96 in a patient's body. For example, one or more balloons may be utilized to align portions 106 and 108 of a blood vessel with a segment 104 which is to be implanted into the blood vessel.

It should be understood that the present invention has a plurality of different features which may be utilized separately or in various combinations. It is also contemplated that the various features of the invention may be utilized with known features from the prior art. Although specific combination of features have been described herein, it is contemplated that other combinations of features will be apparent to those skilled in the art and will be formed.

Furthermore, although certain applications are described herein, those of ordinary skill in the art will appreciate other applications for the present invention. For example, the scaffold can be introduced with a non-surgical procedure by a radiologist or other practitioner rather than a formal surgical procedure. The procedure could utilize MRI guidance (open, standing vertical, etc.), ultrasonic guidance, computer navigation, radiographic guidance, PET scanning. The MRI may be a kinematic MRI to isolate the organ or MRI with external pressure allowing one to visualize the organ or tissue type specifically and then implant the scaffold under a pressurized approach so that the external pressure applied would hold the organ in the position while the scaffold would be stabilized.

In view of the foregoing, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method of building at least a portion of a bone for a patient, the method comprising:
    forming a natural bone scaffold having a plurality of passages through which blood may flow and configured for attachment of different types of stem cells, comprising:
        obtaining natural bone from a body;
        removing tissue and cells from the natural bone to form a porous natural collagen structure defining the plurality of passages of the natural bone scaffold;
        shaping the porous natural collagen structure to correspond to a shape of said at least a portion of a bone of the patient based on a three dimensional image of an area in the patient where the natural bone scaffold is to be positioned;

harvesting stem cells from at least one soft tissue source of the patient;

culturing the stem cells;

positioning the stem cells into the passages of the natural bone scaffold; and exposing the stem cells to at least one environmental condition.

2. The method of claim 1, wherein said positioning the stem cells into the passages comprises positioning more than one type of stem cell into the passages of the natural bone scaffold.

3. The method of claim 1, wherein the stem cells differentiate into osteoblasts.

4. The method of claim 1, wherein the natural bone scaffold is created from natural bone tissue removed from at least one of the patient, another living human, a human cadaver, and an animal.

5. The method of claim 1, wherein the stem cells are harvested from connective tissue of the patient.

6. The method of claim 1, further comprising growing the stem cells positioned in the natural bone scaffold in a controlled biologic environment.

7. The method of claim 1, wherein the natural bone scaffold is created outside an operating room where the natural bone scaffold is to be implanted in the patient.

8. The method of claim 1, wherein at least one of said harvesting the stem cells and positioning the stem cells into the passages of the natural bone scaffold is performed with at least one of a robotic system and a haptic system.

9. The method of claim 1, wherein the natural bone scaffold is configured to connect to a vascular supply of the patient.

10. The method of claim 1, wherein the at least one environmental condition includes at least one of static mechanical forces, dynamic mechanical forces, chemical stimuli, and electromagnetic stimuli.

11. The method of claim 1, wherein the at least one three dimensional image is at least one of a computerized tomographic (CT) scan, magnetic resonance image (MRI), positron emission tomography (PET) scan and ultrasound image.

12. The method of claim 1, wherein the natural bone scaffold is configured to be positioned in the patient using a robotic mechanism.

13. The method of claim 1, wherein the three dimensional image of the area in the patient where the natural bone scaffold is to be positioned is provided by at least one of a computerized tomographic (CT) scan, magnetic resonance image (MRI), positron emission tomography (PET) scan, and ultrasound image.

14. The method of claim 1, wherein the natural bone scaffold is configured to be positioned in the patient through a cannula.

15. A method of creating at least a portion of a bone for a patient, the method comprising:

generating a three dimensional image of an area in the patient where said at least a portion of a bone is to be positioned;

forming a natural bone scaffold having a plurality of passages through which blood may flow and configured for attachment of different types of stem cells, comprising:

obtaining natural bone from a body;

removing tissue and cells from the natural bone to leave a porous natural collagen structure defining the plurality of passages of the natural bone scaffold;

shaping the porous natural collagen to correspond to the three dimensional image of the area in the patient, harvesting stem cells from at least one soft tissue source of the patient;

culturing the stem cells;

positioning the stem cells into the passages of the natural bone scaffold; and exposing the stem cells to at least one environmental condition.

16. The method of claim 15, wherein said positioning the stem cells into the passages comprises positioning more than one type of stem cell into the passages of the natural bone scaffold.

17. The method of claim 15, wherein the stem cells differentiate into osteoblasts.

18. The method of claim 15, wherein said obtaining natural bone from a body comprises removing the natural bone tissue from at least one of the patient, another living human, a human cadaver, and an animal.

19. The method of claim 15, wherein the stem cells are harvested from connective tissue of the patient.

20. The method of claim 15, wherein the natural bone scaffold is formed at a location outside an operating room where the natural bone scaffold is configured to be implanted in the patient.

21. The method of claim 15, wherein at least one of said harvesting the stem cells from the patient and said positioning the stem cells into the passages of the natural bone scaffold is performed with at least one of a robotic system and a haptic system.

22. The method of claim 15, wherein the natural bone scaffold is configured to connect to a vascular supply of the patient.

23. The method of claim 15, wherein the at least one environmental condition includes at least one of static mechanical forces, dynamic mechanical forces, chemical stimuli, and electromagnetic stimuli.

24. The method of claim 15, wherein the at least one three dimensional image is at least one of a computerized tomographic (CT) scan, magnetic resonance image (MRI), positron emission tomography (PET) scan and ultrasound image.

25. The method of claim 15, wherein the natural bone scaffold is configured to be positioned in the patient using a robotic mechanism.

26. The method of claim 15, wherein the three dimensional image of the area in the patient where the natural bone scaffold is to be positioned is provided by at least one of a computerized tomographic (CT) scan, magnetic resonance image (MRI), positron emission tomography (PET) scan, and ultrasound image.

27. The method of claim 15, wherein the natural bone scaffold is configured to be positioned in the patient through a cannula.

28. A method of forming at least a portion of an organ for a patient, the method comprising:

forming a natural organ scaffold defining a plurality of passages through which blood may flow and configured for attachment of different types of stem cells, comprising:

obtaining at least one of a natural organ and a portion of a natural organ from a body;

removing tissue and cells from the at least portion of the natural organ to form a porous natural collagen structure;

shaping the porous natural collagen to an individual configuration corresponding with the shape of at least one of a specific organ and a portion of a specific organ of the patient in a three dimensional image of an area in the patient where the natural organ scaffold is to be positioned;

harvesting stem cells from at least one soft tissue source of the patient;

culturing the stem cells;

positioning the stem cells into the passages of the natural organ scaffold;

exposing the stem cells to by controlling at least one environmental condition.

29. The method of claim 28, wherein more than one type of stem cell is positioned into the passages of the natural organ scaffold.

30. The method of claim 28, wherein the at least one three dimensional image is at least one of a computerized tomographic (CT) scan, magnetic resonance image (MRI), positron emission tomography (PET) scan and ultrasound image.

31. The method of claim 28, wherein the stem cells are harvested from connective tissue of the patient.

32. The method of claim 28, wherein the natural organ scaffold is formed from natural organ tissue removed from at least one of the patient, another living human, a human cadaver, and an animal.

33. The method of claim 28, wherein the natural organ from the body includes at least a portion of a heart, blood vessel, brain, intestine, stomach, adrenal gland, liver, pancreas, skeleton, spinal cord, or bone.

34. The method of claim 28, wherein the at least one environmental condition includes at least one of chemical stimuli, electromagnetic stimuli, static mechanical forces, and dynamic mechanical forces.

35. The method of claim 28 wherein the natural organ scaffold is created at a location spaced from an operating room where the natural organ scaffold is configured to be implanted in the patient.

36. The method of claim 28, wherein the natural organ scaffold is configured to connect to a vascular supply of the patient.

37. The method of claim 28, wherein at least one of harvesting the stem cells from the patient and positioning the stem cells into the pores of the natural organ scaffold is performed with at least one of a robotic system and a haptic system.

38. The method of claim 28, wherein the natural organ scaffold is configured to be positioned in the patient using a robot.

39. The method of claim 28, wherein the three dimensional image of the area in the patient where the natural organ scaffold is to be positioned is provided by at least one of a computerized tomographic (CT) scan, magnetic resonance image (MRI), positron emission tomography (PET) scan and ultrasound image.

40. A method of building an organ of a body for a patient, the method comprising:

providing a pattern corresponding to the body portion to be repaired or replaced;

applying a moldable first material to at least a portion of the pattern;

solidifying the moldable first material with respect to the pattern;

separating the pattern from the solidified moldable first material to form a mold cavity;

injecting a second material with at least one of a chemical blowing agent and an entrained gas into the mold cavity, the second material solidifying into an open cell porous structure; and creating a synthetic single piece scaffold integrally formed from the open cell porous structure solidified inside the mold cavity, the scaffold having a plurality of passages configured to form a network of blood vessels through which blood may flow, the passages created during processing of the scaffold and comprised of the same material as the scaffold, wherein the passages are at least one of arterioles and venules.

41. The method of claim 40, wherein the organ of a body includes an entire organ.

42. The method of claim 40, wherein the organ of a body includes only a portion of an organ.

43. The method of claim 40, wherein the organ of a body includes at least a portion of a kidney.

44. The method of claim 40, wherein the organ of a body includes at least a portion of a heart, blood vessel, brain, intestine, stomach, adrenal gland, liver, pancreas, skeleton, spinal cord, or bone.

45. The method of claim 40, wherein the scaffold includes synthetic collagen.

46. The method of claim 40, wherein the scaffold is at least one of biodegradable and nonbiodegradable.

47. The method of claim 40, wherein the scaffold includes natural collagen.

* * * * *